United States Patent [19]

van Os et al.

[11] 4,132,777

[45] Jan. 2, 1979

[54] ANTIFUNGAL COMPOSITIONS AND METHOD

[75] Inventors: Jan L. van Os, Voorburg; Engbert P. Oldenkamp, Leidschendam; Dirk A. Smink, Leiderdorp, all of Netherlands

[73] Assignee: Gist-Brocades N.V., Delft, Netherlands

[21] Appl. No.: 744,513

[22] Filed: Nov. 24, 1976

[30] Foreign Application Priority Data

Dec. 1, 1975 [GB] United Kingdom ............... 49302/75

[51] Int. Cl.$^2$ .............................................. A61K 35/00
[52] U.S. Cl. ................................................... 424/119
[58] Field of Search .......................................... 424/119

[56] References Cited

U.S. PATENT DOCUMENTS 3,892,850  7/1975  Struyk et al. ........................ 424/119

OTHER PUBLICATIONS

Gregory, Uses and Applications of Chemicals and Related Materials, Reinhold Publishing Corp., N.Y., N.Y. p. 191 (1939).
New Drugs, 1966, Am. Medical Association, Chicago, Ill., p. 61.

*Primary Examiner*—Jerome D. Goldberg
*Attorney, Agent, or Firm*—Hammond & Littell

[57] ABSTRACT

Antifungal compositions useful for the treatment of ringworm and other fungal infections comprising an antifungally effective amount of natamycin and a non-toxic, pharmaceutically acceptable organic acid compound and a suitable liquid carrier which compositions may be sprayed onto the animal, applied by a sponge or by other topical administration and concentrate comprising natamycin and the non-toxic, pharmaceutically acceptable organic acid compound in dry form.

13 Claims, No Drawings

ANTIFUNGAL COMPOSITIONS AND METHOD

STATE OF THE ART

Ringworm infections often occur, especially when cattle or equines are kept indoors. Although generally the disease is not very dangerous and normally cures spontaneously, the animals suffering from the disease are very bad-looking, and consequently the value of the animals becomes less, thus influencing the cattle trade in an undesired manner. Moreover, the disease is a zoonose, i.e. human beings can be infected by contact with the animals.

A number of compositions are known to be useful against the disease, and the compositions are more or less effective. Most of the known compositions, however, are only useful for individual treatments of each ringworm-infected lesion on the animals, so the treatment of large numbers of animals is very laborious and time-consuming, and thus expensive. Another disadvantage of the topical or local treatment of the animals is that it often occurs that, although the treated locations are cured within a reasonable period of time, the disease subsequently appears at other locations on the same animal.

Although, on the other hand, compositions exist that can be sprayed onto the animals, these compositions suffer from the disadvantage that they can irritate the mucous membranes of the eye of animals and human beings, and are sometimes toxic.

OBJECTS OF THE INVENTION

It is an object of the invention to provide a new composition useful against ringworm infections which does not show the disadvantages of the local treatments indicated above, is not irritating to mucous membranes, and cures the animals treated without the risk that the infection can appear at other locations on the animal within a relatively short interval after treatment.

It is another object of the invention to provide a novel method of treating or preventing ringworm and other fungal skin infections of warm-blooded animals and concentrates therefore.

These and other objects and advantages of the invention will become obvious from the following detailed description.

THE INVENTION

The novel antifungal compositions of the invention are comprised of an antifungally effective amount of natamycin, a non-toxic, pharmaceutically acceptable organic acid compound and a liquid carrier. The compositions preferably have an acid pH. The compositions are useful for the treatment of ringworm infections, mainly those caused by *Trichophyton verrucosum* in cattle, and by *T. equinum* or *Microsporum equinum* in equines, particularly horses. Not only cattle and equines can suffer from these and analogous infections, but also small domestic animals and human beings can be attacked and the disease is enzootic, i.e. spreads within large groups of animals. The compositions may also be used for the treatment of other fungal diseases, e.g. Aspergillus infections in poultry and equines.

Natamycin [also called pimaricin, cf. Merck Index, 8th hd. (1968) page 834] per se is also effective against ringworm infections but suffers from the same disadvantages as indicated above when used topically and surprisingly can be formulated into a new composition useful for the treatment of large numbers of animals with the additional advantage that re-appearance of the disease soon after treatment is avoided. The spraying of a composition containing natamycin alone, i.e. without the organic acid compound, has been carried out on animals. It has been found, however, that such compositions often show too low an activity to be effective against ringworm when sprayed.

The liquid carrier should be a liquid which does not deleteriously affect the skin and other mucous membranes of animals or humans, and water is the preferred carrier. Such a composition is very useful for the treatment of large numbers of animals, especially animals kept indoors, e.g. by spraying the composition onto the animal. Spraying of the composition has the advantage that the animal is treated as a whole, so that locations that are not visibly attacked by ringworm are also treated, thus avoiding the risk that ringworm will occur at other locations after treatment of visibly attacked lesions. Spraying of the composition has the further advantage that the cow-shed, stable, etc., in which the animals are kept, is also disinfected to a certain extent. For example, when treating horses, it may be advisable to treat also their harness to prevent an infected harness being a cause of further infections.

Non-toxic, pharmaceutically acceptable acid compounds for incorporation in the compositions of the invention are those pharmaceutically acceptable acid compounds, (i.e. compounds, not harmful to animals and human beings when applied exteriorly to them in concentrations in which they are effective in combination with natamycin in the treatment of ringworm infections) preferably capable of giving the final suspension or solution a pH within the range of 2.0 to 4.5, prefeably 2.5 to 3.5. Examples of suitable acids are ascorbic acid, citric acid, dihydroxytartaric acid, glutaric acid, iodacetic acid, itaconic acid, malic acid, mandelic acid, oxalic acid, salicylic acid, succinic acid and $\alpha$- and meso-tartaric acid. The most preferred acid is citric acid, especially in its anhydrous form. Other useful acid compounds are alkali metal and ammonium salts thereof, e.g. monosodium citrate, monosodium tartrate and potassium tetroxalate.

The compositions are preferably formulated as an aqueous suspension just before use, and these suspensions preferably contain about 50 ppm to about 300 ppm of natamycin, more preferably about 100 ppm to about 200 ppm of natamycin, and an amount of acid compound sufficient to bring the pH of the final solution or suspension within the range of 2.0 to 4.5, preferably 2.5 to 3.5. For citric acid, these amounts range from about 400 ppm to about 1600 ppm preferably about 600 ppm to about 1200 ppm.

Additional materials may also be present in the compositions such as a wetting agent, for example a non-ionic surfactant such as a fatty alcohol polyethylene oxide condensate, or an anionic surfactant such as an alkali metal salt, e.g. sodium salt, of a fatty alcohol sulfate or an alkyl benzene sulfonate; an anti-oxidant such as lactose; or a well-dispersible filler such as certain kinds of finely divided clays or silicon oxides or hydrous oxides, or mixtures of two or more of those substances.

The ready-for-use composition is preferably prepared starting from a concentrate. Since the natamycin is relatively unstable in aqueous solutions or suspensions, the concentrate is preferably a dry form, and for that reason an acid compound is preferably used which is solid at ambient temperatures. Citric acid is very well suited for this requirement. The concentrate may be prepared by combining the solid acid compound and the solid natamycin and, if desired, additional materials in their dry forms, in the required amounts.

It is also possible to prepare a combined package containing the materials in several containers, e.g. one container for the natamycin and another container for a corresponding amount of acid. The contents of the containers may then be mixed to make a concentrate before diluting it to the desired concentration, but it is also possible to dissolve or suspend each of the components in a small amount of water and dilute the aqueous suspension obtained to the desired concentration.

A useful method of making a package of two containers containing the natamycin and the acid is selecting such containers, e.g. glass bottles or vials, having necks of the same diameter in which case the package also contains advantageously a connecting tube with both ends open and preferably provided with a brim in the middle of the tube length, fitting into the necks of the bottles. Before use the connecting piece is placed on one bottle or vial after opening it, and then the neck of the other bottle is placed on the free end of the connecting piece. In this situation the contents of the bottles or vials may be mixed by shaking, and after mixing the bottles or vials are disconnected, whereafter the contents may be diluted to the desired concentration. For this purpose, the natamycin is advantageously kept in one bottle in dry form, whereas the other bottle may contain the acid compound in liquid or dissolved form. Packages of this kind also constitute a feature of the invention.

The present invention also includes within its scope a concentrate comprising solid natamycin and a solid pharmaceutically acceptable acid compound in the desired amounts, if desired, together with additional materials. Such concentrates, when stored properly, may be kept for several months without substantial deactivation of the natamycin.

The ready-for-use preparation may be prepared by dissolving or suspending the concentrate in an appropriate amount of water, but, preferably, the concentrate is dissolved or suspended first in a small amount of water, and the solution or suspension obtained is then diluted to the desired concentration. After preparing the ready-for-use composition, the animals, livestock such as cattle and horses, are treated with the composition. When cattle are to be treated, the composition is preferably sprayed onto the animals, for example, by means of a sprayer, e.g. one carried on a man's back. The use of the sprayer has the additional advantage that, when the animals are sprayed, the cow-shed in which they are kept is also disinfected to some extent thereby promoting effective, relatively long-term control of the disease. When treating equines, e.g. horses, the composition is preferably applied by means of a sponge or the like. It is advisable to treat also the horses' harnesses. Other warm-blooded animals as small domestic animals and human beings may be treated with the composition of the invention. If necessary, the composition may also be applied by other topical treatment.

The composition may further be used for the treatment of other fungal disease, e.g. Aspergillus infections in poultry and equines, and shows a greater activity than natamycin compositions without the acid compound.

In the following examples there are described several preferred embodiments to illustrate the invention. However, it is to be understood that the invention is not intended to be limited to the specific embodiments.

EXAMPLE 1

A composition containing 100 ppm of natamycin and 800 ppm of citric acid was prepared as follows:

1 g of natamycin, 10 mg of sodium lauryl-sulfate, 4 mg of Aerosil (finely divided silica), 1 g of lactose and 8 g of anhydrous citric acid were mixed together and the mixture was placed in a 100 ml dark brown glass bottle. Under these conditions, the mixture may be stored at ambient temperature for several months without risk of the natamycin losing its activity. The bottle containing the mixture of natamycin and citric acid was filled to about half its volume with water, and the contents were mixed thoroughly. The mixture was poured into a plastic bucket with a volume of somewhat more than 10 liters, which contained about 10 liters of water and the contents of the bucket were mixed by simply stirring with a rod. The contents of the bucket were then poured into a sprayer.

Another composition containing 200 ppm of natamycin alone was made up in a similar manner, starting from twice the amount of natamycin, sodium lauryl-sulfate, Aerosil and lactose.

Various experiments were carried out in various cow-sheds using the said compositions. In Experiment 1 (cf. the Table hereafter), a cow-shed containing 128 cows was treated. The cows were divided into two separate groups: (A) 92 cows were treated with a composition containing 100 ppm of natamycin and 800 ppm of citric acid, and (B) 36 cows served as a control group and were not treated.

In Experiment 2, a group (A) of 17 cows was treated with a composition containing 200 ppm of natamycin and 800 ppm of citric acid, and a group (B) of 12 cows was not treated.

In Experiment 3, a group (A) of 80 cows was treated with a composition containing 200 ppm of natamycin, and a group (B) of 25 animals was treated with an aqueous solution containing 1% of Defungit [a commercial fungicide composition containing 3-benzyl-5-carboxymethyl-4H-1,3,5-thiadiazin-2-one as the active principle].

In Experiment 4, a group (A) of three cows was treated with a solution of 100 ppm of natamycin in water, and a group (B), also three cows, was treated with a composition containing 100 ppm of natamycin and 800 ppm of citric acid.

In Experiment 5, a group (A) of 101 cows was treated with a solution of 200 ppm of natamycin and a group (B) of 111 cows was treated with a composition consisting of an aqueous solution of 200 ppm of natamycin and 800 ppm of citric acid.

In Experiment 6, a group (A) of 46 cows was treated with a composition containing 100 ppm of natamycin and 800 ppm of citric acid, and a group (B) of 41 cows was treated with a composition containing 200 ppm of natamycin and 800 ppm of citric acid.

The results are shown in the following Table in which the signs have the following meanings:

− = no effect;
+ = a moderate effect;
++ = a good effect;
+++ = a very good effect;
( ) = also occurring.

TABLE

| Experiment | | natamycin ppm | citric acid ppm | Defungit % | Number of cows | weeks after treatment | | |
|---|---|---|---|---|---|---|---|---|
| | | | | | | 2–3 | 4–5 | 6–7 |
| 1 | A | 100 | 800 | — | 92 | +;++ | ++;+++ | +++ |
| | B | — | — | — | 36 | — | — | — |
| 2 | A | 200 | 800 | — | 17 | ++ | +++ | +++ |
| | B | — | — | — | 12 | — | — | — |
| 3 | A | 200 | — | — | 80 | + | ++ | +++ |
| | B | — | — | 1 | 25 | — | + | ++ |
| 4 | A | 100 | — | — | 3 | + | + | ++ |
| | B | 100 | 800 | — | 3 | + | ++ | ++;+++ |
| 5 | A | 200 | — | — | 101 | + | +;(++) | ++;(+++) |
| | B | 200 | 800 | — | 111 | +;(++) | ++;(+++) | +++;(++) |
| 6 | A | 100 | 800 | — | 46 | ++;(+) | +++;(++) | +++;(++) |
| | B | 200 | 800 | — | 41 | ++;(+) | +++;(++) | +++;(++) |

The results in the Table show that an aqueous suspension of natamycin has a somewhat better effect than an aqueous solution of 1% of Defungit (twice the advised concentration in Experiment 3), that the compositions containing both natamycin and citric acid are better and give a quicker effect than the compositions containing natamycin without the citric acid (Experiments 4 and 5) and that a composition of 100 ppm of natamycin and 800 ppm of citric acid has about the same effect as a composition of 200 ppm of natamycin and 800 ppm of citric acid (Experiment 6). It may also be seen that a composition containing 100 ppm of natamycin and 800 ppm of citric acid is better than a composition containing 200 ppm of natamycin without citric acid (compare Experiments 6A and 5A).

An aqueous composition according to the invention containing 100–200 ppm of natamycin together with, for example, 800 ppm of citric acid is thus normally a good composition for the treatment of animals suffering from ringworm infection. It can also be deduced from the Table that the compositions of the invention have a better effect than Defungit in a 1% aqueous solution.

EXAMPLE 2

In a stable with 19 horses and two foals, 15 horses and one foal suffered from a ringworm infection showing one or more lesions. The healthy animals were not treated, but the infected animals were treated with the composition of the invention containing 100 ppm of natamycin and 800 ppm of citric acid (calculated as anhydrous acid). The composition was applied by treating the lesions with a sponge wetted with the composition and the results are shown in the following Table, in which

| | | | |
|---|---|---|---|
| o means one lesion | | — means deteriorated | |
| oo means 2 to 10 lesions | | + means infection stationary | |
| ooo means more than 10 lesions | | ++ means distinctly improved | |
| = means no lesions (anymore) | | +++ means recovered | |
| T means treatment | | | |

| | Day of treatment | After 3 weeks | After 10 weeks |
|---|---|---|---|
| 6 horses | ooo/T | =/+++ | |
| 2 horses | ooo/T | ooo/++/T | =/+++ |
| 1 horse | ooo/T | ooo/—/T | oo/++ |
| 5 horses | oo/T | =/+++ | |
| 1 horse | oo/T | o/++ | oo/++ |
| the foal | o/T | =/+++ | |

Thus, the Table shows that 11 horses and the foal recovered in 3 weeks, two horses were cured partially in 3 weeks but recovered in 10 weeks after repeated treatment, one horse showed more lesions after 3 weeks but was cured partially in 10 weeks after repeated treatment, and one horse cured partially in 3 weeks but was still not recovered in 10 weeks, although his skin looked healthier.

The present invention also includes within its scope a method for the treatment of ringworm infections and other fungal infections in man and domestic animals, more particularly cattle and equines, e.g. horses, which comprises applying to man or a domestic animal a composition comprising an effective amount of natamycin and a pharmaceutically acceptable organic acid compound, preferably an aqueous composition comprising at least the two aforesaid ingredients. Liquid compositions of the invention hereinbefore described may be employed in the said method.

Various modifications of the compositions of the invention may be made without departing from the spirit or scope thereof and it should be understood that the invention is to be limited only as defined in the appended claims.

We claim:

1. An antifungal composition useful for the treatment of ringworm and other fungal infections consisting essentially of an antifungally effective amount of natamycin and a sufficient amount of citric acid to give the final suspension or solution a pH within the range of 2.0 to 4.5 and a liquid carrier.

2. An antifungal dry concentrate for the preparation of the composition of claim 1 consisting essentially of natamycin and sufficient amount of citric acid to give a solution of the concentrate a pH value of 2.0 to 4.5.

3. The concentrate of claim 2 which also contains at least one member of the group consisting of a wetting agent, an antioxidant and a dispersible filler.

4. A package concentrate of claim 2 wherein the natamycin and the organic acid compound are in different combined containers.

5. The composition of claim 1 wherein the pH range is 2.5 to 3.5.

6. The antifungal composition of claim 1 wherein the natamycin concentration is about 50 to about 300 ppm.

7. The antifungal composition of claim 1 wherein the citric acid concentration is about 400 to about 1600 ppm.

8. The composition of claim 7 wherein the concentration is 600 to 1200 ppm.

9. The composition of claim 6 wherein the concentration is 100 to 200 ppm.

10. The composition of claim 1 wherein the citric acid is anhydrous.

11. A method of treating and preventing topical fungal infections in warm-blooded animals comprising topically applying to warm-blooded animals an antifungally effective amount of a composition of claim 1.

12. The method of claim 11 wherein the composition is applied by spraying as a solution or dispersion onto cattle.

13. The method of claim 11 wherein the composition is applied by sponging to equines as an aqueous solution or dispersion.

* * * * *